United States Patent [19]
Grothoff et al.

[11] Patent Number: 5,857,991
[45] Date of Patent: Jan. 12, 1999

[54] DEVICE FOR APPLYING MEDICATION FLUID ON MUCUS MEMBRANE IN BODY CAVITIES

[76] Inventors: Hans Grothoff, Pulverstrasse 35, 44225 Dortmund; Hans-Peter Harke, Theodor-Fahr-Strasse 27, 22419 Hamburg; Frank Hennig, Kammerloh 54, 24558 Henstedt-Ulzburg; Gerd Neumann, Hamburger Strasse 210, 22083 Hamburg, all of Germany

[21] Appl. No.: 694,670

[22] Filed: Aug. 9, 1996

[30] Foreign Application Priority Data

Aug. 10, 1995 [DE] Germany .......................... 195 30 879.4

[51] Int. Cl.⁶ .................................................. A61M 35/00
[52] U.S. Cl. .......................... 604/2; 604/311; 128/200.14; 128/200.22; 222/575; 222/566; 222/478; 239/302; 239/337; 239/571
[58] Field of Search ................................ 604/1–3, 36, 37, 604/38, 39, 310, 311; 128/200.14, 200.21, 200.22; 222/575, 566, 478, 481; 239/145, 302, 337, 571

[56] References Cited

U.S. PATENT DOCUMENTS

| | | | |
|---|---|---|---|
| 1,018,193 | 2/1912 | Hinkle | 128/200.14 |
| 1,082,142 | 12/1913 | Spardel | 604/39 |
| 1,494,985 | 5/1924 | Beck | 604/36 |
| 2,265,080 | 12/1941 | Mezey | 604/36 |
| 2,596,597 | 5/1952 | Raymond et al. | 128/200.14 |
| 3,784,063 | 1/1974 | Otis et al. | 604/310 |
| 3,938,898 | 2/1976 | Reitknecht | 604/2 |
| 4,892,526 | 1/1990 | Reese | 604/310 |
| 4,950,231 | 8/1990 | Liu | 604/39 |

*Primary Examiner*—Mark O. Polutta
*Assistant Examiner*—Dennis Ruhl
*Attorney, Agent, or Firm*—Michael J. Striker

[57] ABSTRACT

A device for applying medication fluid on mucus membrane in interior of body cavities has a manually actuatable pump element mountable on a medication supply container for discharging a medication fluid and having an outlet, an insertion tube having one end connected with the outlet and provided with a through going longitudinal opening, a distributor body connected with an opposite end of the insertion tube and having an outer shape and a volume to correspond to a body cavity to be treated, the distributor body having a plurality of outlet openings distributed over its outer surface and communicating through an interior of the distributor body with the insertion tube so that a medication fluid supplied under pressure is a discharged from the outlet openings over an outer surface of the distributor body.

21 Claims, 5 Drawing Sheets

FIG. 6
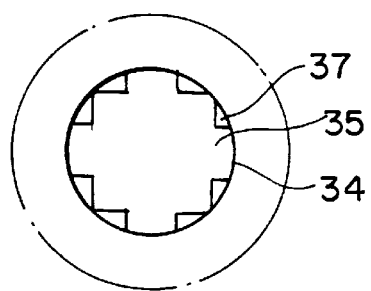
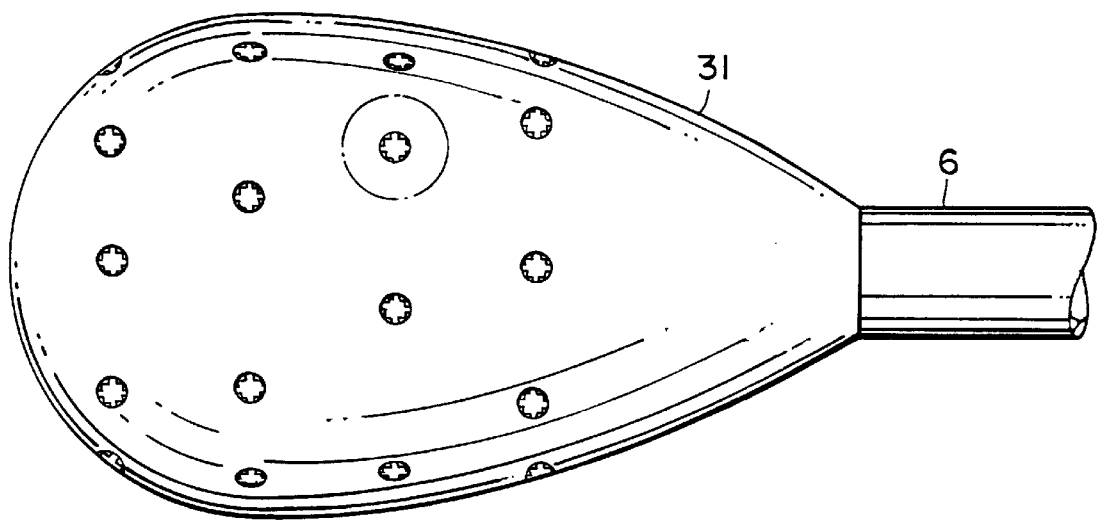
FIG. 5

DEVICE FOR APPLYING MEDICATION FLUID ON MUCUS MEMBRANE IN BODY CAVITIES

BACKGROUND OF THE INVENTION

The present invention relates to a device for applying medication fluids on a mucus membrane in inner body cavities, in particular in oral, vaginal, and anal regions, for all prophylactic and therapeutical applications of fluids.

When such body zones are treated, it is extremely important that the treatment be performed in a simple and inexpensive manner both in private places as well as in medical practices and hospitals. A further important point is that the medication fluids must be applied uninterruptedly and completely so as to cover the whole mucus membrane region even with small dosages.

For a special therapy, for example in vaginal region, an extensive wetting of the region to be treated is extremely important. For example, sexually transmitted infections in vaginal regions are treated by gynecologists with special chemotherapeutic media. The gynecologist can apply medication fluids during such treatment on wads, spraying heads or by rinsing. Moreover, it is often desirable to provide an accompanying application by patients themselves, which can be repeated in non-stationary conditions. For such a self-application there are no available devices.

The device for rinsing the vaginal region is known, which has a bellows vessel with an insertion tube screwed in it and provided with several openings on its tip. With this device, it is possible to perform rinsing, or in other words application of great quantities of fluid on the corresponding mucus membrane region. However, it is not possible to apply small doses with simultaneous complete distribution on the respective region. A further disadvantage is that since only great fluid quantities can be utilized and they must be then discharged to a greater part, the application can be performed only with special provisions, for example in a bath tub which is not filled with water, so as to allow discharge of excessive preparation.

Furthermore, with known devices a single rinsing is only available, since, after introduction of the insertion tube in the vaginal region and compression of the bellows container it is not always guaranteed that before removal of the device a return suction affect occurs by unauthorized expansion of the bellows container. This can lead to entry of the body fluid into the device and a repeated use of the device without preceding sterilization, which of course is highly undesirable.

SUMMARY OF THE INVENTION

Accordingly, it is an object of the present invention to provide a device for application of medication fluid on the mucus membrane in the interior of body cavities, which avoids the disadvantages of the prior art.

More particularly, it is an object of the present invention to provide a device for applying medication fluid on mucus membrane in body cavities, which provides for an efficient application of small medication fluid quantities, in particular in fine stepped doses.

In keeping with these objects and with others which will become apparent hereinafter, one feature of present invention resides, briefly stated, in a device for application of medication fluids to mucus membrane in the interior of the body cavities, which has a manually control pumping means on a medication supply container for discharging medication fluid under pressure from an outlet, and insertion tube connected with the outlet and having a longitudinal opening, a distributor body connected with the opposite end of the insertion tube and corresponding to an outer shape and volume of a body cavity to be treated as well as provided with a plurality of outlet openings distributed over its outer surface, and the outer openings communicate through an interior space of the distributor body with the insertion tube, so that under the pressure the supplied medical liquid is discharged from the outlet openings in a distributed fashion over the surface of the distributing body.

In the inventive device, the manually controllable pumping element provided on the medication supply container discharges the medication fluid under pressure. The outlet of the pumping element is connected with an insertion tube whose opposite end is connected with the distributor body. The distributor body is formed so that its outer shape and sizes correspond to the body cavity to be treated and has a plurality of outlet openings distributed over the outer surface and communicating with the insertion tube through an inner space of the distributor body. By actuating of the pumping element, an application of the medication fluid finely distributed by the distributor body is performed through the plurality of outlet openings into the interior of the body cavity so that also small fluid quantities can be applied in the body cavity in a distributed fashion.

In accordance with a preferable embodiment of the present invention, a return flow preventing feature is provided, so that the medication fluid can be discharged, but no return suction of the fluid into the distributor body can occur. This can be obtained by providing any one-way valve. In an advantageous embodiment of the present invention, the pump element is formed by a finger pressure-actuated pressure built-up fine automizer pump, which has an over pressure function so that a liquid discharge is released after exceeding a structurally predetermined compression threshold. The predetermined compression threshold in typical cases is between 2 and 20 bar. In this case it is guaranteed that the medication fluids enters the distributor body with relatively high pressure and is ejected uniformly through the outlet openings. On the one hand, in a simple manner the situation is prevented that at a corresponding time point a negative pressure can be produced in the distributor body so that the fluid can be sucked back from outside in the distributor body. It is thereby guaranteed in a simple manner that the distributor body remains sterile and a multiple use is safe for the same patient. Moreover, such automizer pumps can be selected that with the actuation of the push button a very small fluid quantity is supplied with a typical value in the region of 0.1–2 ml. This simplifies a finely dosed discharge and application of the medication fluid.

In order to provide a fine spraying and distribution of the medication fluid, the outlet openings preferably have a small diameter at an average less than 200 um. It is especially advantageous when the diameter is equal to between 5 um and 15 um. Such fine outlet openings can be produced for example by a laser drilling of a synthetic plastic hollow body. Alternatively, the distributor body can be produced of a microporous material, for example from open-cell foam, to obtain a fine distribution of the medication fluid over the micropores.

In a preferable embodiment of the present invention, the outlet openings in the distributor body are produced by providing a plurality of openings leading to the inner space of the distributor body and inserting in these openings insert bodies, so as to reduce the cross-sectional area of the corresponding opening and therefore to form outlet openings of a smaller size. Therefore a fine spray discharge of the medication fluid is obtained without drilling of the openings with extremely small diameters.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 5 is a view of a further embodiment of the distributor body;

FIG. 6 is an enlarged detailed view of a surface region of an outlet opening on the distributor body of FIG. 6.

DESCRIPTION OF PREFERRED EMBODIMENTS

Figure 1:
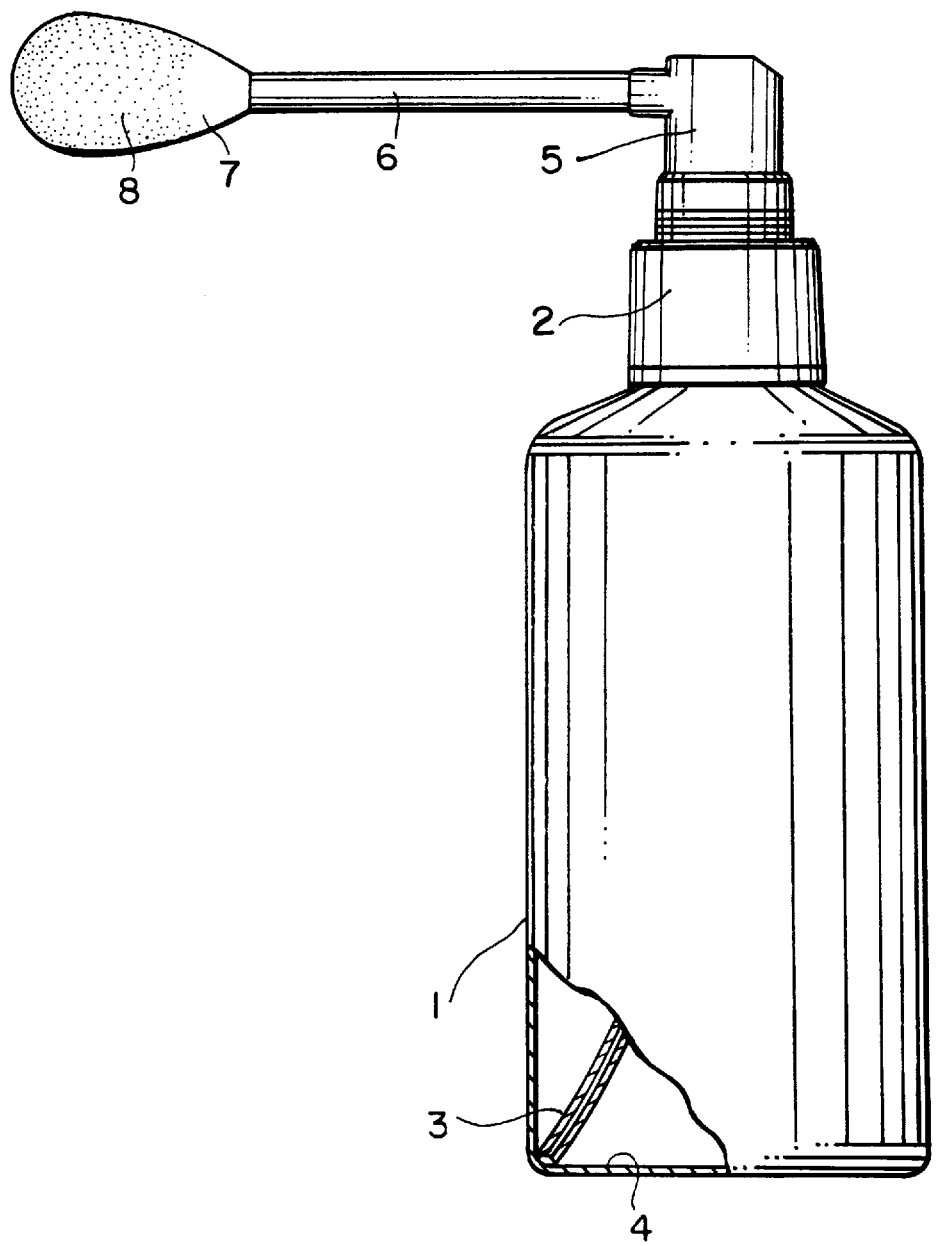
FIG. 1 is a partially sectioned side view of a device for application of a medication fluid in body cavities in accordance with the present invention.

FIG. 1 shows a device for application of medication fluid in body cavities on a general view. The device has a pump element 2 which can be formed as a finger pressure-actuated automizer pump, and a supply container 1 on which the pump element is mounted. The pump element 2 has an outlet located opposite to a pressing member 5. An insertion tube 6 provided with a throughgoing longitudinal opening is connected with the outlet. A distributor body 7 is provided on the other end of the insertion tube 6. Its inner space communicates with the longitudinal opening of the insertion pipe 6. The distributor body 7 has a plurality of outlet openings 8 communicating with the inner space of the distributor. The pump element 2 is provided with a raiser tube 3 extending to a bottom 4 of the supply container 1 so as to provide a complete emptying of the supply container 1.

Figure 2:
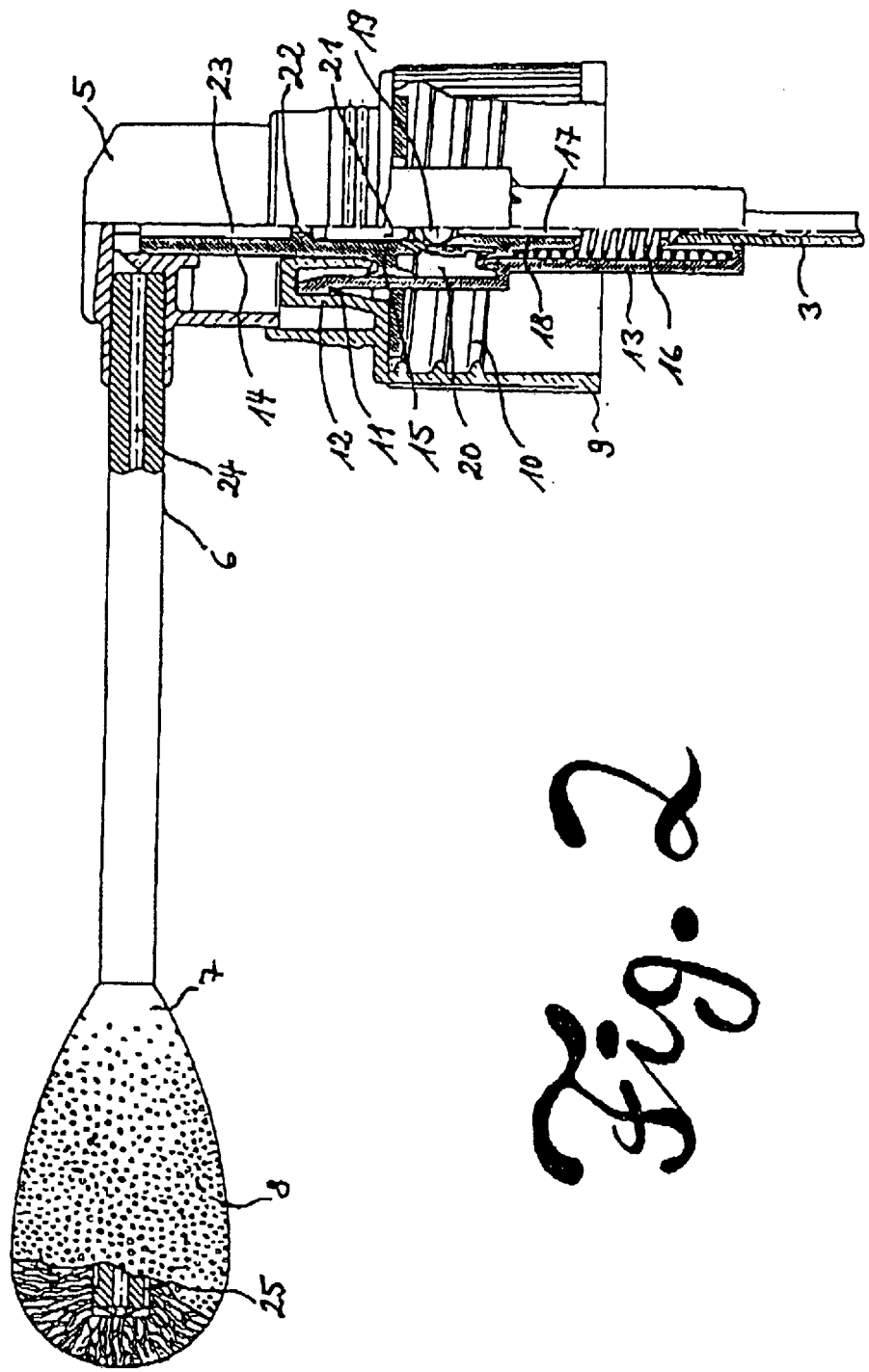
FIG. 2 is a partial sectioned, partial view of the inventive device for FIG. 1, which shows a pumping element, an insertion tube and a distributor body.

FIG. 2 shows the construction of a finger pressure-actuated automizer pump. The screw body 9 provided with inner threads 10 serves for mounting on a neck of the supply container 1 having a corresponding thread. A dome 12 of the screw body 9 is connected with a cylinder 13 by a snap connection 11, and the raiser tube 3 is held in the cylinder by pressure seat. A shaft 14 of a working piston 15 extends outwardly through an opening in the dome 12. The pressing element 5 is arranged on the shaft 14. The fluids during the return stroke of the pressing member 5 actuated by the pre-tensioned spring 16 is supplied under negative pressure through the raiser tube 3 and an inner opening 17 of a control piston 18 with lifting of a return ball 19, into a compression chamber 20 arranged between the working piston 15 and the control piston 18 in an upper region of the cylinder 13 having a greater diameter.

By the actuation of the pressing member 5, the control piston 18 advances in accordance with the differential piston principle relative to the working piston 15 as long as the fluid pressure acting on the control piston 18 exceeds the counterpressure of the spring 16 and opens the throughgoing opening 2 in the working piston 15 by pulling back the blocking pin 21 fixedly connected with the control piston 18. The pre-tensioned fluid contained in the compression chamber 20 flows through the connecting opening 23 in the pressing member 5 and from there through the longitudinal opening 24 of the insertion tube 6 flows into the inner space of the distributor body 7.

The drop-shaped distributor body 7 in the embodiment shown in FIG. 2 is composed of a microporous material, for example of open-pore foam material or sintered body. In view of the relatively great total surface of the pores, the pressure building in the inner chamber of the distributor body 7 by the pump element is relatively low, and therefore the fluid exits in form of a film which is uniformly distributed over the whole outer surface of the distributor body. This embodiment is especially suitable for handling of mucus regions by the distributor body 7 directly and with a complete contract.

Figure 3:
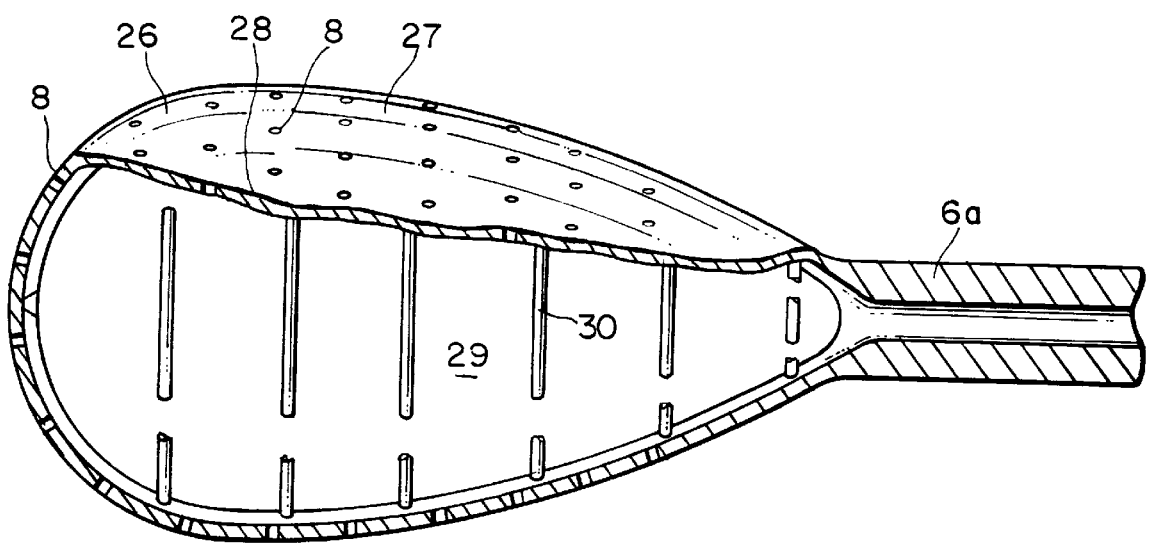
FIG. 3 is a partially sectioned view of an alternative embodiment of the distributor body in accordance with present invention.

An advantageous embodiment of the distributor body characterized by a simple varying of the application characteristics of the fluid is shown in FIG. 3. The distributor body is composed of two halves 26 and 27 which are inserted in one another and sealed, and also provided with a plurality of outlet openings 8. The joint 28 is arranged in the region of the greater diameter of the drop-shaped distributor body and can be formed by snapping, welding or adhesive connection. The rear half of the distributor body can be fitted on the insertion tube 6. However, it is advantageous when the insertion tube end region 6a is formed directly on the rear half 27 of the distributor body as shown in FIG. 3.

The distributor body is provided with a filler body 29 for obtaining in its inner chamber as little dead volume as possible. The filling body 29 is held at a uniform distance to the inner wall of the distributor body halves via webs 30. The distributor body 29 is formed advantageously either as a fluid-tight hollow body or as a closed-pore foam body for minimizing the total weight of the device.

The outlet openings 8 are produced preferably by laser drilling. The number and size of the openings determines the discharge of the medication fluid, from the formation of individual jets with a long distance action to the film-shaped surface wetting of the distributor body, depending on the requirements of the respective application. For example, with a perforation size of 20 um and a number of perforations of 100 with a low viscous fluid, a substantially jet-shaped discharge is provided, while with a double opening diameter of 40 um or an increase in the perforation number to 400 a film-like wetting is performed. With a corresponding number of various opening diameters, a combined effect can be produced. For example, the combination of the openings with a diameter of 5 um and 20 um with a corresponding number of the openings leads to a distributor body which produces both a jet-like liquid discharge and simultaneously a film-like surface webbing.

Figure 4:
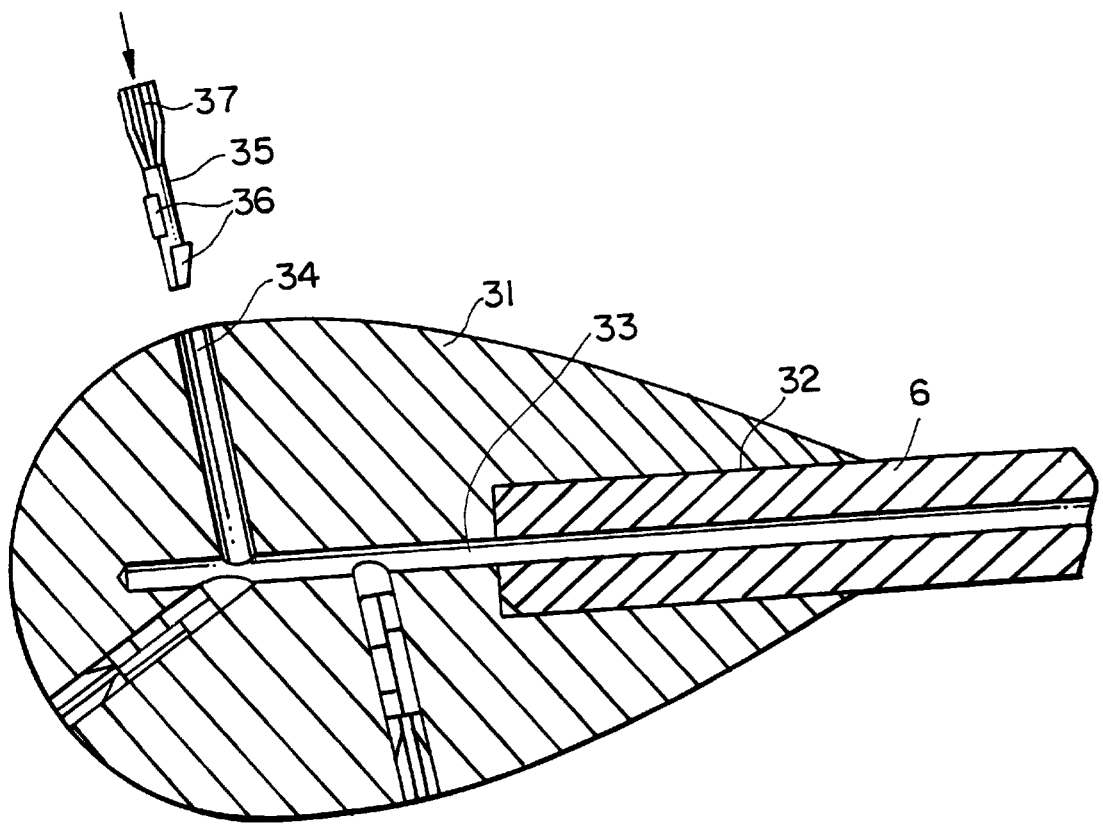
FIG. 4 is a sectional view of a further alternative embodiment of the distributor body.

However, in the above described embodiments, the manufacture is relatively expensive since a laser drilling device and further tools and molds are needed. In the embodiment shown in FIGS. 4–6 the device can be produced simpler. The distributor body 31 in this embodiment is made of a solid material, preferably a synthetic plastic material in a material-removing manner on automatic lathes, starting from a strand material. After drilling of the receiving opening 32 for the insertion tube 6 and the subsequent central opening 33, the desired drop-shaped outer contour is machined and the body is removed. The openings 34 are preferably produced fully automatically on single or multiple-spindle drilling automatic machines and communicates with a central opening 33. A pressing member 35 is pressed into each opening 34. It is oversized relative to the opening 34 and thereby reliably fixed in the opening. An additional safety can be obtained by arranging of holding claws 36 on the lower part of the shaft.

The pressing body 30 is provided in a front region with recesses in form of axially extending grooves 37. Their geometrical cross-section is formed in dependence on the technical features of the manufacturing process. The triangular shape of the grooves shown in FIGS. 6 results from the manufacturing possibilities of the injection-molding methods for synthetic plastics. The axially extending grooves form outlet passages remaining in the opening 34. The grooves 34 on the pressing body 35 reduce the cross-sectional area of each opening 34 and form a plurality of substantially smaller outlet openings 8. In this way in the mechanically is simply produced openings with a relatively great diameter, very fine outlet openings can be made.

It will be understood that each of the elements described above, or two or more together, may also find a useful application in other types of constructions differeng from the types described above.

While the invention has been illustrated and described as embodied in device for applying medication fluid on mucus Membrane in body cavities, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A device for applying medication fluid on mucus membrane in interior of body cavities, comprising a manually actuatable pump element; a medication supply container on which said pump element is mounted for discharging a medication fluid and having an outlet; an insertion tube having one end connected with said outlet and provided with a longitudinal opening; a distributor body connected with an opposite end of said insertion tube and having an outer shape and a volume to correspond to a body cavity to be treated, said distributor body having a plurality of outlet openings distributed over its outer surface and communicating through an interior of said distributor body with said insertion tube so that a medication fluid supplied under pressure is discharged from said outlet openings over an outer surface of said distributor body, said distributor having an inner chamber; and a fluid-tight filler body which is separate from said distributor body and is located in said inner chamber of said distributor body and leaving a space for a flow from said insertion tube to said outlet openings.

2. A device as defined in claim 1, wherein said pump element is formed so that the medication fluid is discharged in dosed quantities.

3. A device as defined in claim 1, wherein said pump element is formed as a finger pressure-actuated pressure build-up automizer pump.

4. A device as defined in claim 1, wherein said pump element is formed as a pressure automizer operating under the action of a gas pressure.

5. A device as defined in claim 1, wherein said pump element is formed so that the medication fluid is discharged under a pressure of 2–20 bar.

6. A device as defined in claim 1, wherein said outlet openings of said distributor body have an average diameter of less than 200 um.

7. A device as defined in claim 1, wherein said distributor body is formed as a hollow body composed of a synthetic plastic material and provided with an outer wall having a plurality of the outlet openings with diameters in the region of between 5 um and 50 um.

8. A device as defined in claim 1, wherein said distributor body is composed of two halves which are sealingly inserted in one another.

9. A device as defined in claim 1, wherein said filler body is formed as a closed-pool foam body.

10. A device as defined in claim 1, wherein said filler body is formed as a hollow body.

11. A device as defined in claim 1, wherein said distributor body is composed of a microporous material with micropores forming said outlet openings.

12. A device as defined in claim 11, wherein said microporous material of said distributor body is an open-cell foam material.

13. A device as defined in claim 1, wherein said distributor body and said insertion tube are directly connected with one another.

14. A device as defined in claim 13, wherein said distributor body and said insertion tube are formed of one-piece with one another.

15. A device as defined in claim 1, wherein said pump element and said insertion tube are directly connected with one another.

16. A device as defined in claim 1, wherein said distributor body is composed of a microporous material with a plurality of pores which form said outlet openings.

17. A device as defined in claim 16, wherein said distributor body is composed of an open-pore foam microporous material with said plurality of pores which form said outlet openings.

18. A device as defined in claim 16, wherein said distributor body is formed as a sintered body composed of the microporous material with said plurality of pores which form said outlet openings.

19. A device for applying medication fluid on mucus membrane in interior of body cavities, comprising a manually actuatable pump element; a medication supply container on which said pump element is mounted for discharging a medication fluid and having an outlet; an insertion tube having one end connected with said outlet and provided with a longitudinal opening; a distributor body connected with an opposite end of said insertion tube and having an outer shape and a volume to correspond to a body cavity to be treated, said distributor body having a plurality of outlet openings distributed over its outer surface and communicating through an interior of said distributor body with said insertion tube so that a medication fluid supplied under pressure is discharged from said outlet openings over an outer surface of said distributor body; and one way valve means preventing a return flow from said distributor body opposite to a pumping direction.

20. A device for applying medication fluid on mucus membrane in interior of body cavities, comprising a manually actuatable pump element; a medication supply container on which said pump element is mounted for discharging a medication fluid and having an outlet; an insertion tube having one end connected with said outlet and provided with a longitudinal opening; a distributor body connected with an opposite end of said insertion tube and having an outer shape and a volume to correspond to a body cavity to be treated, said distributor body having a plurality of outlet openings distributed over its outer surface and communicating through an interior of said distributor body with said insertion tube so that a medication fluid supplied under pressure is discharged from said outlet openings over an outer surface of said distributor body; and a pressing body inserted in each of said openings so as to reduce an area of said openings.

21. A device for applying medication fluid on mucus membrane in interior of body cavities, comprising a manually actuatable pump element; a medication supply container on which said pump element is mounted for discharging a medication fluid and having an outlet; an insertion tube having one end connected with said outlet and provided with a longitudinal opening; a distributor body connected with an opposite end of said insertion tube and having an outer shape and a volume to correspond to a body cavity to be treated, said distributor body having a plurality of outlet openings distributed over its outer surface and communicating through an interior of said distributor body with said insertion tube so that a medication fluid supplied under pressure is discharged from said outlet openings over an outer surface of said distributor body, said pump element and said insertion tube being connected with one another; and a flexible hose for connecting said pump element with said insertion tube.

* * * * *